United States Patent [19]

McGinley

[11] Patent Number: 5,250,019
[45] Date of Patent: Oct. 5, 1993

[54] APPARATUS FOR STEREOTACTIC RADIOSURGERY

[75] Inventor: Patton H. McGinley, Stone Mountain, Ga.

[73] Assignee: Emory University, Atlanta, Ga.

[21] Appl. No.: 990,557

[22] Filed: Dec. 14, 1992

Related U.S. Application Data

[63] Continuation of Ser. No. 532,057, Jun. 1, 1990, abandoned.

[51] Int. Cl.$^5$ .............................................. A61N 5/00
[52] U.S. Cl. ........................................... 600/1; 5/622
[58] Field of Search ..................... 600/1; 128/774, 752, 128/377; 5/600–622

[56] References Cited

U.S. PATENT DOCUMENTS

| | | |
|---|---|---|
| 309,701 | 7/1971 | Stoltser . |
| 341,269 | 12/1972 | Kogan . |
| 1,113,138 | 9/1984 | Pakhomov . |
| 3,506,826 | 4/1970 | Kösters .............................. 250/55 |
| 3,627,250 | 12/1971 | Pegrum ............................. 248/324 |
| 3,652,077 | 3/1972 | James ................................ 269/322 |
| 3,783,251 | 1/1974 | Pavkovich ......................... 235/151 |
| 3,794,840 | 2/1974 | Scott ................................. 250/363 |
| 3,848,132 | 11/1974 | Foderaro ........................... 250/439 |
| 3,859,982 | 1/1975 | Dove ................................. 128/2 R |
| 4,044,265 | 8/1977 | Schmidt ............................ 250/439 |
| 4,071,231 | 1/1978 | Kok .................................. 269/325 |
| 4,481,657 | 11/1984 | Larsson ............................. 378/209 |
| 4,653,083 | 3/1987 | Rossi ................................ 378/196 |
| 4,681,308 | 7/1987 | Rice .................................. 269/322 |

OTHER PUBLICATIONS

Lutz et al., "A System for Stereotactic Radiosurgery With A Linear Accelerator", *Journal of Radiation Oncology Biological Physics*, 14: 373–381 (1988).

McGinley, P. H., *Medical Physics*, "A Patient Rotator for Stereotactic Radiosurgery", 16:674, Abstract No. WP1-9 (Jul./Aug. 1989).

McGinley et al., "A Patient Rotator for Stereotactic Radiosurgery", *Phys. Med. Biol.*, 35:649–657 (1990).

*Primary Examiner*—Lee S. Cohen
*Assistant Examiner*—J. P. Lacyk
*Attorney, Agent, or Firm*—Needle & Rosenberg

[57] ABSTRACT

An apparatus for performing stereotactic radiosurgery using a stationary radiation source is comprised of a frame, a platform rotatably connected to the frame about a vertical rotational axis, a patient receiving menas, a means for rotating the platform and a means for adjusting the head of the patient to permit intersection of the radiation beam central axis with the vertical rotational axis at the location of the target site that is the subject of the radiosurgery. A method for performing stereotactic radiosurgery using the apparatus is also provided.

3 Claims, 8 Drawing Sheets

DOSE PROFILES FOR THREE COLLIMATOR DIAMETERS: 1, 2, AND 3 cm BASED ON FILM MEASUREMENTS

SAGITTAL DOSE DISTRIBUTION FOR 2cm COLLIMATOR AND O=60°

SAGITTAL DOSE DISTRIBUTION FOR .2cm COLLIMATOR
AND O = 35°, 60°, 80°

TRANSVERSE DOSE DISTRIBUTION FOR 2 cm COLLIMATOR AND O = 35°, 60°, 80°

SAGITTAL DOSE DISTRIBUTION RIGHT FRONT QUADRANT, 2 cm COLLIMATOR AND O = 35°, 60°, 80°

TRANSVERSE DOSE DISTRIBUTION RIGHT FRONT QUADRANT, 2 cm COLLIMATOR AND O = 35°, 60°, 80°

APPARATUS FOR STEREOTACTIC RADIOSURGERY

This application is a continuation of application Ser. No. 07/532,057, filed Jun. 1, 1990, now abandoned.

BACKGROUND OF THE INVENTION

This invention relates to a novel apparatus for rotating a patient during stereotactic radiosurgery and a novel method for performing stereotactic radiosurgery.

There is at present an increasing interest by a number of radiation therapy groups to carry out stereotactic radiosurgery using radiation from sources such as medical accelerators (x-ray beams) or cobalt 60 units (gamma ray beams). The primary goal of such therapy is to deliver high doses of radiation to small target volumes within the brain and at the same time minimize the radiation dose to all points outside the target volume.

Several techniques have been developed for isocentrically mounted linear accelerators in which the gantry is moved during therapy. One of these, the dynamic rotational method, is carried out by arcing the gantry and moving the treatment table at the same time. Podgorsak et al., "Dynamic Stereotactic Radiosurgery." *Int. J. Radiat. Oncol. Biol. Phys.* 14:115–125 (1988). A second technique, the multiple arc method, employs several non-coplanar arcs with the treatment table moved between arcs. Lutz et al., "A System for Stereotactic Radiosurgery with a Linear Accelerator," *Int. J. Radiat. Oncol. Biol. Phys.* 14:373–381 (1988); Colombo et al., "External Stereotactic Irradiation by Linear Accelerator," *Neurosurgery* 16:154–160 (1985); Hartman et al., "Cerebral Radiation Surgery Using Moving Field Irradiation at a Linear Accelerator Facility," *Int. J. Radiat. Oncol. Biol. Phys.* 11:1185–1192 (1985).

A common requirement for the conventional multiple arc and dynamic rotation methods is that the axis of rotation of the treatment table intersect the isocenter of the gantry for all positions of the gantry and treatment table used for patient therapy. That requirement adds to the complexity of patient positioning. Additionally, neither technique allows a full 360° rotation of the gantry due to possible gantry collisions with the treatment table, patient, and the stereotactic equipment. A full rotation of the gantry is desirable because it tends to produce isodose contours that are more symmetrical and smooth than those generated by multiple arcs.

Moreover, in these conventional methods, the patient is in a supine position on a treatment table with his head held immobile by a stereotactic head ring which is screwed into the patient's skull. Any unintentional movement of the treatment table may cause injury to the patient because the stereotactic head ring that is screwed into the patient's skull is mounted to the floor and cannot move coincidently with the treatment table.

A further shortcoming of existing rotation methods and associated respective apparatus relates to a tendency for the gantry to move after the drive motor is stopped. Some accelerators have been equipped with collision switches that turn off power to the gantry drive motor in case of a failure of the gantry to stop at the intended angle or in case of a mistake in setting the gantry or table stop angles. Because of the inertia created when the gantry is arced, the gantry tends to move as much as 10° after the drive motor is stopped, thereby creating a condition in which the gantry may collide with the patient or stereotactic equipment.

SUMMARY OF THE INVENTION

The disadvantages of the prior art are overcome by the present invention which comprises a platform rotatably connected to a frame which is bolted to the floor. A patient receiving means is mounted to the platform which rotates about a vertical rotational axis. A stereotactic system mounted on the platform provides a means for adjusting the patient with respect to the vertical rotational axis to permit intersection of the radiation beam central axis from a stationary radiation source with the vertical rotational axis of the platform at the location of the target site that is the subject of the radiosurgery.

The method of the invention provides a means for performing stereotactic radiosurgery on a patient who may be rotated 360° during the surgery which is performed using a stationary source of radiation. A stationary source of radiation is provided which emits a radiation beam of controlled intensity having a radiation beam central axis. The patient is positioned in a patient receiving means that is connected to a platform that rotates about a vertical rotational axis. Using a stereotactic system, the patient is positioned so that the vertical rotational axis intersects the radiation beam central axis at the target site of the radiosurgery. The patient is then irradiated while being rotated about the vertical rotational axis.

It is, therefore, an object of the present invention to provide an improved apparatus for rotating a patient during stereotactic radiosurgery. It is another object of the invention to provide a method of performing stereotactic radiosurgery by administering radiation to a target point in a patient wherein during the administration, the gantry is stationary. A further object of the invention is to provide an apparatus capable of rotating a patient 360° such that the axis of rotation intersects the central axis of the radiation beam at the target site of the radiosurgery during the 360° rotation.

These and other objects will be apparent from the following detailed description of the present invention.

BRIEF DESCRIPTION OF THE FIGURES OF DRAWINGS

DETAILED DESCRIPTION OF THE PREFERRED EMBODIMENTS

Figure 1:
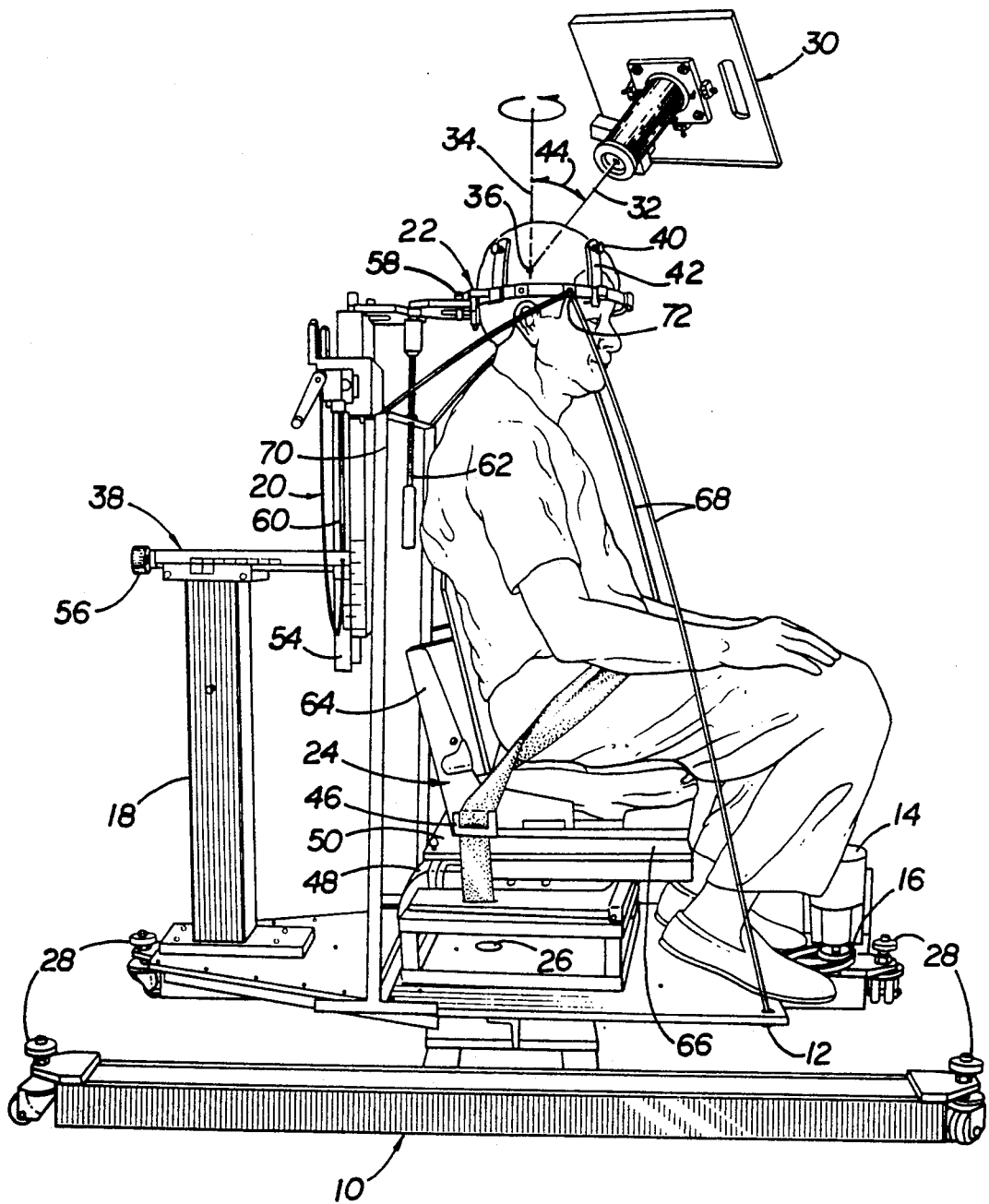
FIG. 1 is a perspective view of the present invention with a patient seated in the patient receiving means.

Referring to FIG. 1, a frame 10 is secured to the floor at points 28. Platform 12 is rotatably connected to the frame 10 at some point 26 which determines the location of the vertical rotational axis 34. Motor 14 provides the rotational drive means to rotate platform 12 about axis 34 through associated, conventional means, including belt 16. A patient receiving means 24 is connected to platform 12 and includes a means for adjusting the patient in both the vertical and horizontal directions. The patient receiving means 24 may be a seat having a vertical member 64 and a horizontal member 66. Means for adjusting the patient in the horizontal direction may include a horizontal adjustment support 48 over which the patient receiving means platform 50 may be adjustably positioned. The patient receiving means may be racheted (not shown in the drawings) to be adjusted vertically at a desired height above platform 12. Additionally, means, such as waist belt 46, may be provided to help maintain the patient in the proper adjusted position.

Stereotactic system 38 is comprised of support 18, which mounts the stereotactic system 38 to the platform 12 and stereotactic head ring 22, which is adjustably connected to support 18 through stereotactic adjustment means 20. Stereotactic adjustment means 20 provides means for adjusting the stereotactic head ring 22 in both the horizontal and vertical directions. The means for adjusting the stereotactic head ring 22 in the horizontal direction may include the adjustment of horizontal bar 56 by a threaded screw mechanism (not shown). The stereotactic head ring may be adjusted in the vertical direction by the adjustment of vertical bar 54 using threaded bar 60. Horizontal bar 56 and vertical bar 54 have locational indicia for positioning stereotactic head ring 22 which is removably attached to the remainder of the stereotactic system by attachment pin 58.

Stereotactic head ring 22 is mounted to the patients head by means of pins such as pin 40 which extends through arm 42 which, in turn, is connected to the main body of stereotactic head ring 22. To prevent the movement of stereotactic head ring 22, threaded support 62 is adjusted by screwing through yoke 70 which extends to and is bolted to platform 12. Additional support may be provided by use of support bars 68 which extend from yoke 70 to the stereotactic head ring 22 to which each support bar 68 is connected, for example, at point 72. Support bars 68 further extend from stereotactic head ring 22 to platform 12 to which support bars 68 are securely attached.

Radiation source 30 is a conventional apparatus and is fixed to provide a radiation beam 32 having a radiation beam central axis which intersects vertical rotational axis 34 at target 36 site which is the target site of the stereotactic radiosurgery.

To perform stereotactic radiosurgery by the method of the present invention, stereotactic head ring 22 may be removed from stereotactic system 38 at attachment pin 58. Stereotactic head ring 22 is attached to the patient's head by means of pins such as pin 40. The three dimensional coordinates of the target site of the radiosurgery are determined by standard imaging techniques such as CT scanning, angiography or MR scanning. The stereotactic system is adjusted to correspond to these three dimensional coordinates. The desired angle 44 is achieved by adjusting the position of radiation source 30. The alignment of the radiation source and the stereotactic system may be checked radiographically using a target ball (not shown in the drawings).

Once the proper alignment is achieved, the patient is placed in patient receiving means 24 which may be adjusted vertically or horizontally to accommodate the individual patient. Stereotactic head ring 22 is affixed to stereotactic system 38 by pin 58. The desired radiosurgery is then performed by irradiating the target site 36 with radiation beam 32 while simultaneously rotating platform 12.

The following example is provided to further illustrate the claimed invention and is not intended to limit the claimed invention in any way.

EXAMPLE

The stereotactic head ring is mounted on a floor support which is attached to the rotator platform. The gantry of the accelerator is rotated to angles in the range of 35° to 80° with respect to the vertical and is held stationary when the patient is treated. The frame is bolted to the floor at a location such that the central axis of the radiation beam intersects the vertical rotation axis at the isocenter point. Any motion of the isocenter that occurs when the gantry angle is changed can be compensated for by a slight shift of the rotator base. Three orthogonal drives on the floor support are used to position the ring and patient's head so that the target center is at the isocenter. A medical accelerator, such as model MX-6700 TM available from Siemens, is used to produce a 6 MV x-ray beam for stereotactic radiosurgery. The accelerator is equipped with a collimator and is used to produce x-ray beams of circular cross section with diameters from 1 cm to 3 cm in steps of 0.25 cm at the isocenter.

The performance of the collimator was evaluated by measuring beam profiles, tissue maximum ratios (TMR), and total scatter factors ($S_t$) Rice et al., "Measurements of Dose Distributions in Small Beams of 6 MV x-rays," *Phys. Med. Biol.* 32:1087–1099 (1987). These measurements were carried out using a polystyrene phantom in which KODAK ® XV-2 film or a PTW 30-334 TM parallel plate chamber was placed. The water equivalent depth was calculated from the depth in the plastic phantom by multiplication of a scaling factor suggested in the AAPM TG-21 protocol. AAPM, "A protocol for the determination of absorbed dose from high-energy photons and electron beams," *Medical Phys* 10:741–771 (1983). All film dosimetry measurements were corrected for nonlinearity by use of a calibration curve obtained from the film batch used. A CMS DYNAS-CAN TM film scanner was used to obtain the dose distribution produced by irradiation. The PTW 30-334 TM ionization chamber was selected for use in this work due to its small sensitive volume (3 mm diameter and 2.0 mm plate spacing) which makes is useful for measurements in small radiation fields. Rice et al., supra.

Localization of the target volume and center to be treated is achieved by use of the stereotactic system, such as that available from Brown-Roberts-Wells (BRW TM), in conjunction with angiographs or CT scans obtained with a Philips Tomoscan LX TM at a slice thickness of 1.5 mm. Only a brief description of the localization technique will be given since detailed information can be found in the literature. Lutz et. al., supra.

A CT localizer device is attached to the head ring and the coordinates of the target center in terms of the CT coordinate system are established. The CT coordinates are then transformed to the stereotactic coordinate system by means of the computer which is a component of the BRW TM stereotactic system. A similar procedure is used to evaluate the target center coordinates when angiography is used.

Alignment of the isocenter, rotator axis, and target center is evaluated by use of the LUTZ TM target simulator supplied with the BRW TM stereotactic system. This device consists of a small steel sphere that is attached by two adjustable rods to a sector of a head ring. The center of the ball can be positioned at the coordinates of the target center by use of the BRW TM phantom base which consists of a pointer that can be set to the target coordinates by vernier devices and a ring for attachment of the target simulator. Adjustment of the phantom pointer in the vertical directions is made to account for the radius of the target simulator ball. The steel ball simulator is manipulated so that it is just above the phantom base pointer and is then locked in position with respect to the head ring. The target simulator is then transferred to the floor stand and by adjustment of the orthogonal drives to the target coordinates the center of the ball is moved to the isocenter. A film holder is attached to the collimator so the film is located in the radiation beam beyond the target ball. The x-ray beam is used to expose the film to check the alignment of the target ball and radiation beam. Eight exposures are made at increments of 45° of platform rotation of each gantry angle that will be used for therapy with the film being moved to a new position before each exposure. Verification of the alignment of the isocenter, target center, beam central axis, and rotator axis is assured if the target ball remains in the center of the exposed region for each rotator and gantry position.

A phantom fabricated from LUCITE® with the same size and shape as the head section of the RANDO TM phantom was employed to test the target localization technique and to evaluate the dose distribution resulting from radiational therapy. Slots were cut in the phantom so that film could be placed in the sagittal, coronal, and transverse plane. Dosimeter slots not employed for a test run were filled with thin Lucite sheets to eliminate air spaces. In order to mark the target center for a localization test a straight pin was pushed through the film and most of the shaft was cut off. A CT or angiogram was then taken of the phantom and coordinates of the pinhead were determined. By means of this method dose distribution measurements and target localization tests could be carried out for target centers located at various points in the brain.

Results

Figure 2:
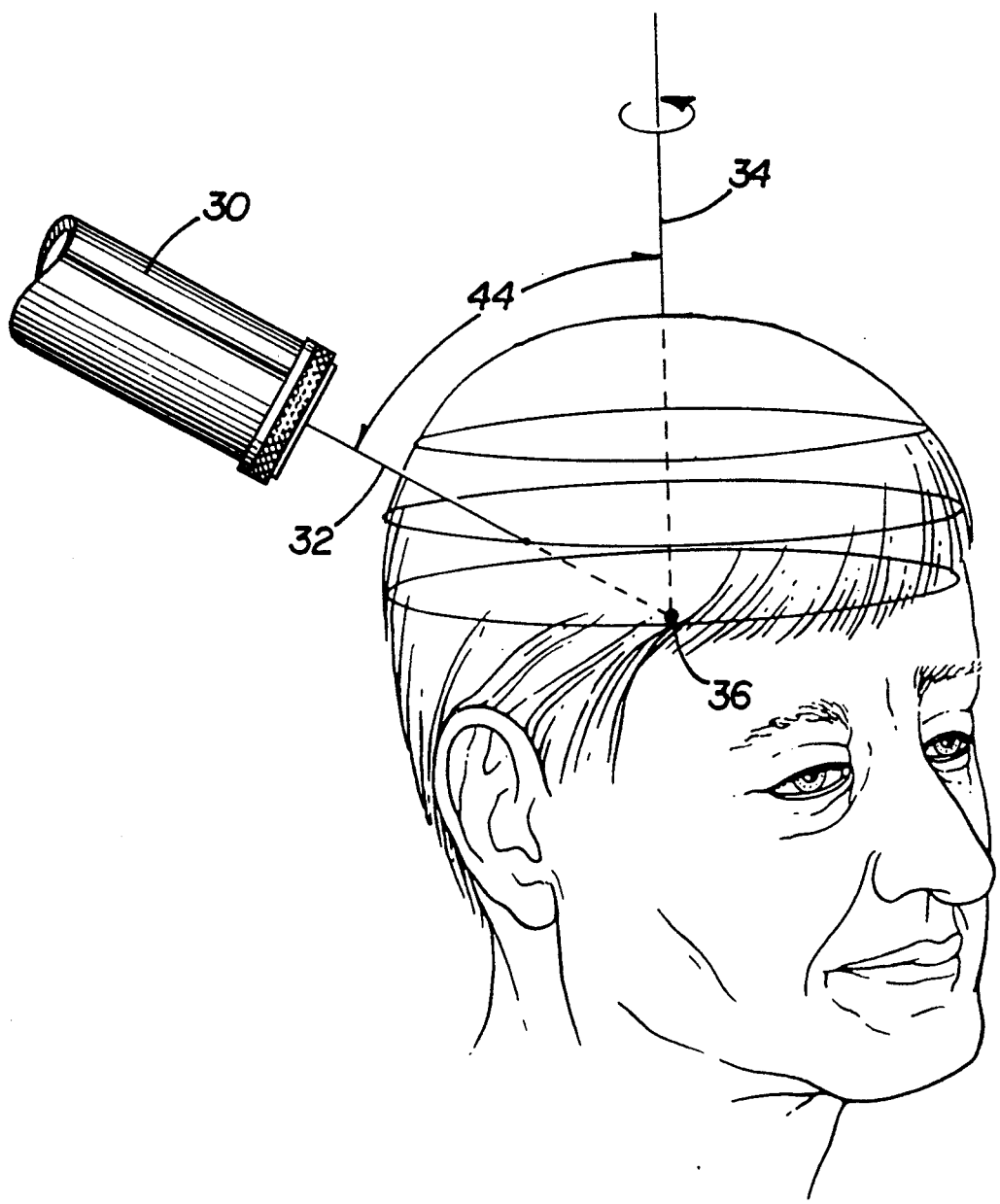
FIG. 2 is a perspective view showing the beam entry path, rotational axis and beam central axis.

Beam profiles based on film measurements were obtained for each collimator. FIG. 2 shows the percent dose as a function of distance from the central axis of the beam for the 1.0, 2.0, and 3.0 cm diameter collimators at a water equivalent depth of 5 cm in the polystyrene phantom. Penumbra distances (90% to 20%) of 3.0, 3.7, and 4.0 mm were found for the 1.0, 2.0 and 3.0 cm diameter collimators respectively at a depth of 5 cm. Table 1 presents the 50% beam width ($W_d$) evaluated at a depth of 5 cm and the total scatter factor ($S_t$) as a function of collimator diameter. Tissue maximum ratios measured at a number of depths for different collimators are given in Table 2.

TABLE 1

Physical parameters of radiation beams used for stereotactic radiosurgery

| Collimator Size (cm) | $W_d$ 50% beam width at isocenter (cm) | $S_t$ Total Scatter function |
|---|---|---|
| 1.0 | 0.90 | 0.808 |
| 1.5 | 1.40 | 0.875 |
| 2.0 | 1.77 | 0.898 |
| 2.5 | 2.35 | 0.906 |
| 3.0 | 2.85 | 0.917 |

TABLE 2

Tissue maximum ratios (TMR) for various beam sizes.

| Depth (cm) | TMR Beam Size (cm) | | | | |
|---|---|---|---|---|---|
| | 1.0 | 1.5 | 2.0 | 2.5 | 3.0 |
| 1.6 | 1.0000 | 1.0000 | 1.0000 | 1.0000 | 1.0000 |
| 5 | 0.858 | 0.868 | 0.874 | 0.888 | 0.889 |
| 10 | 0.672 | 0.690 | 0.697 | 0.708 | 0.713 |
| 15 | 0.528 | 0.545 | 0.557 | 0.565 | 0.566 |
| 20 | 0.425 | 0.436 | 0.450 | 0.453 | 0.455 |

Figure 3:
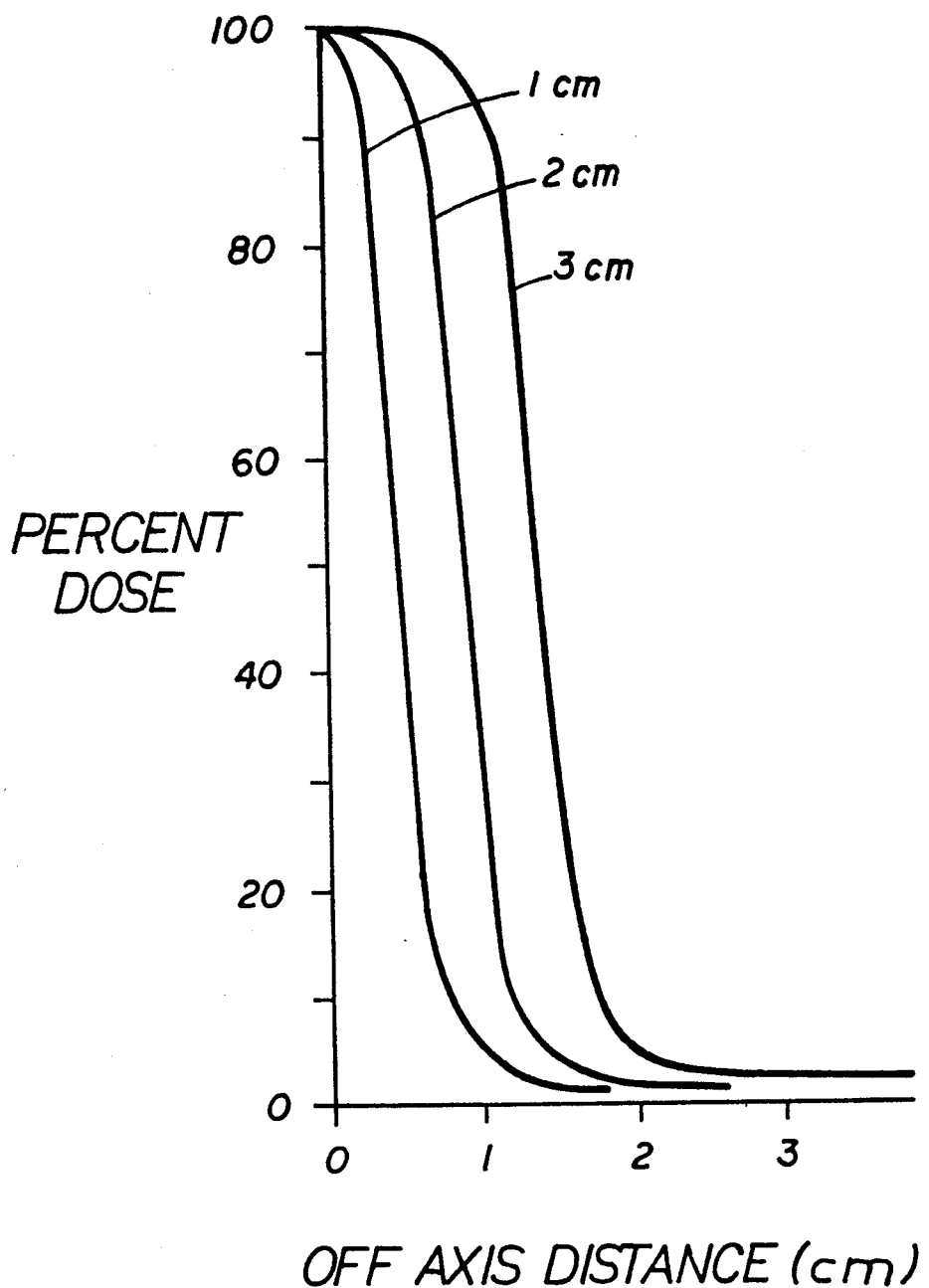
FIG. 3 is a graph depicting the dose profile for 1, 2, and 3 cm collimators measured at a depth of 5 cm by use of the film method.
Figure 4:
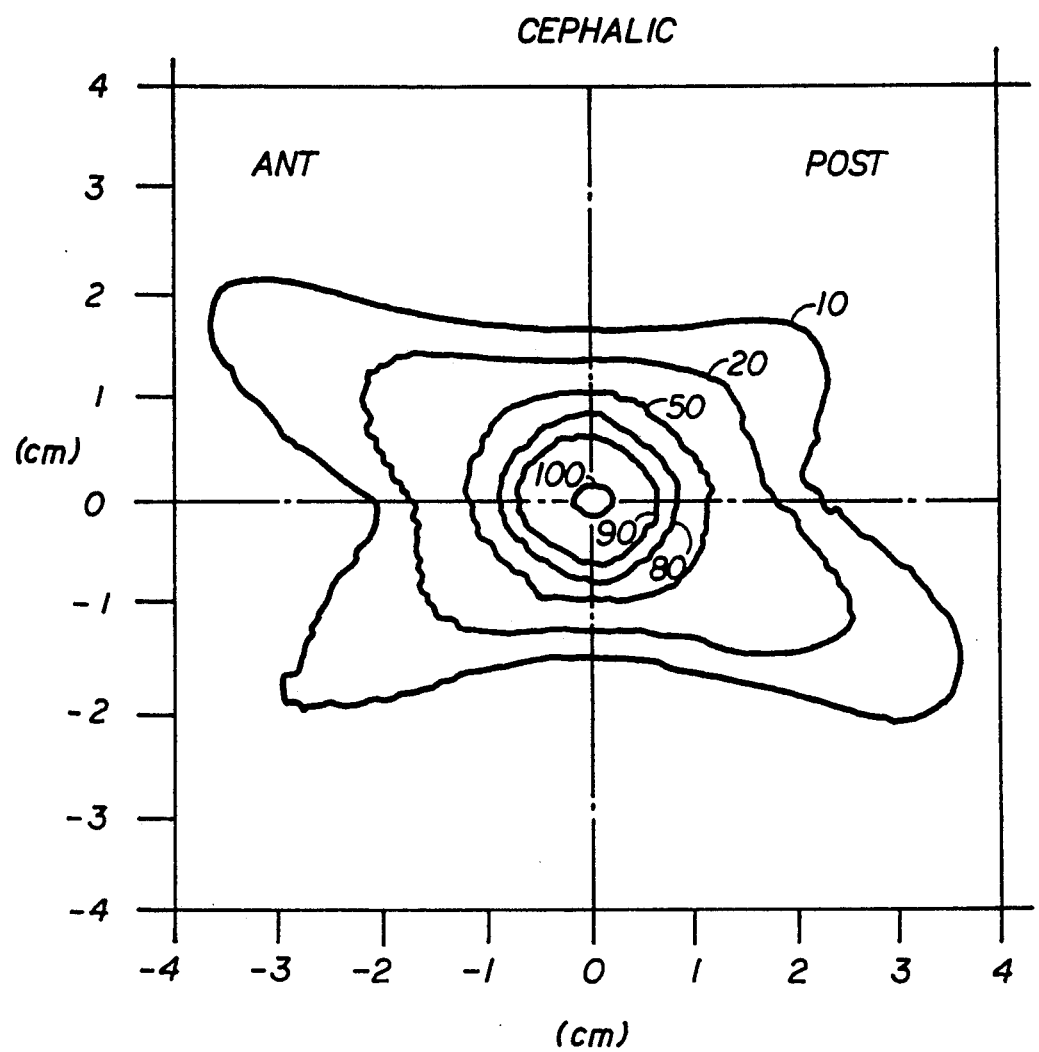
FIG. 4 is a graph depicting the sagittal dose distribution produced by rotation of phantom.
Figure 5:
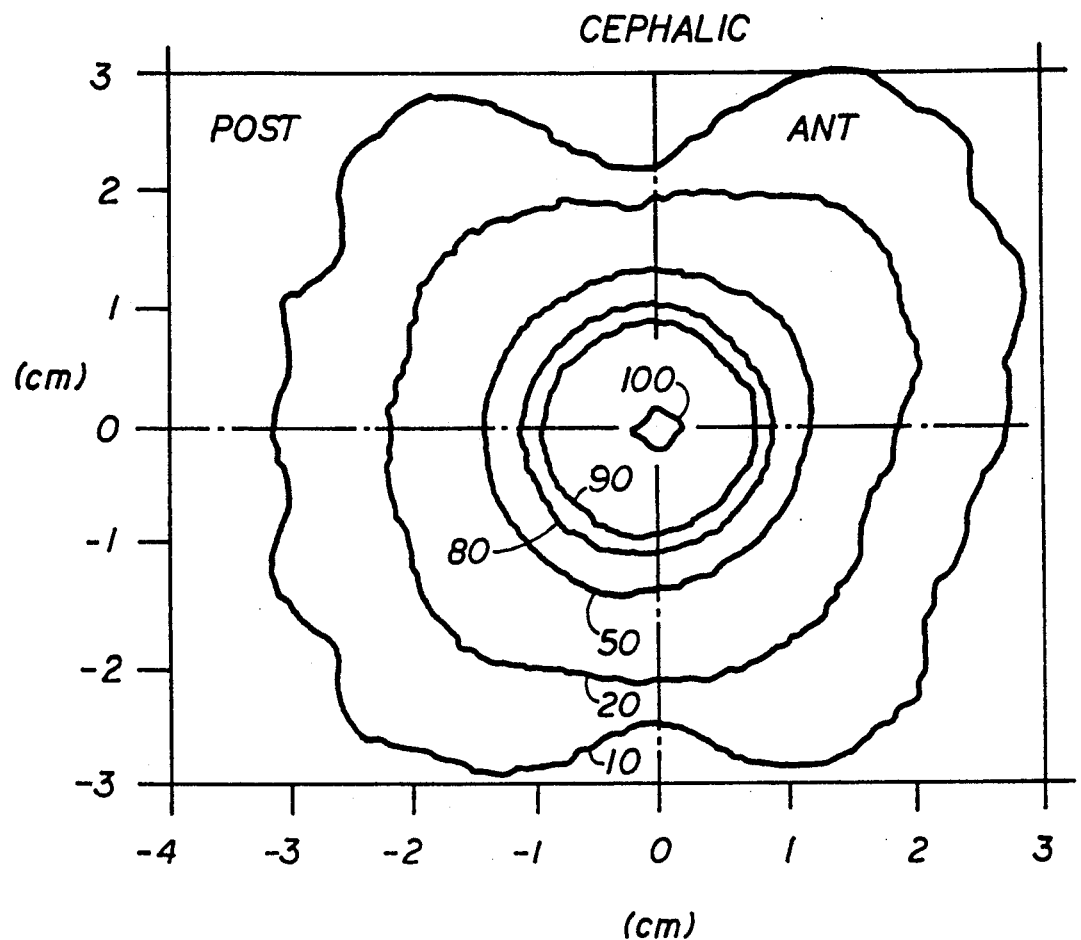
FIG. 5 is a graph depicting the sagittal dose distribution produced by use of 35°, 60°, and 80° gantry angles with the 2 cm diameter collimator for a target point located near the center of the brain.

A spherical high dose region (90% and 80%) can be generated when a gantry angle of 60° with respect to the vertical is employed with a patient rotation. FIG. 3 shows the sagittal dose distribution produced when the 2 cm collimator is used with a 60° gantry angle to treat a lesion near the center of the brain and Table 3 presents the shallowest and steepest dose fall off outside the target volume for several combinations of gantry angles. As can be seen in Table 3, the dose fall off distance can be reduced by the use of three gantry angles (335°, 60°, 80°) in place of a single gantry angle while maintaining the same sphere shape at high isodose levels. FIGS. 4 and 5 show the isodose distributions measured with film in the transverse and sagittal planes for a target point located near the center of the brain and treated by positioning the gantry at angles of 35°, 60° and 80° with respect to the vertical. An equal number of monitor units were used for each angle and the dose rate produced by the accelerator was low enough to allow at least four complete rotations of the phantom for each of the three gantry angles.

TABLE 3

Minimum and maximum dose falloff distances outside target region located near the center of the brain.

| Gantry angle(s) (cm) | Collimator diameter | Min/Max Distance (cm) | | |
|---|---|---|---|---|
| | | 90 to 50% | 90 to 20% | 90 to 10% |
| 60° | 1 | 0.3/0.4 | 0.5/1.3 | 0.7/2.7 |
| | 2 | 0.4/0.5 | 0.6/2.1 | 1.0/3.4 |
| | 3 | 0.5/0.7 | 0.9/3.2 | 1.5/5.2 |
| 35°, 60°, 80° | 1 | 0.3/0.35 | 0.7/1.0 | 1.0/1.8 |
| | 2 | 0.5/0.5 | 1.1/1.4 | 1.2/2.4 |
| | 3 | 0.5/0.6 | 1.3/2.1 | 1.7/3.0 |

Figure 6:
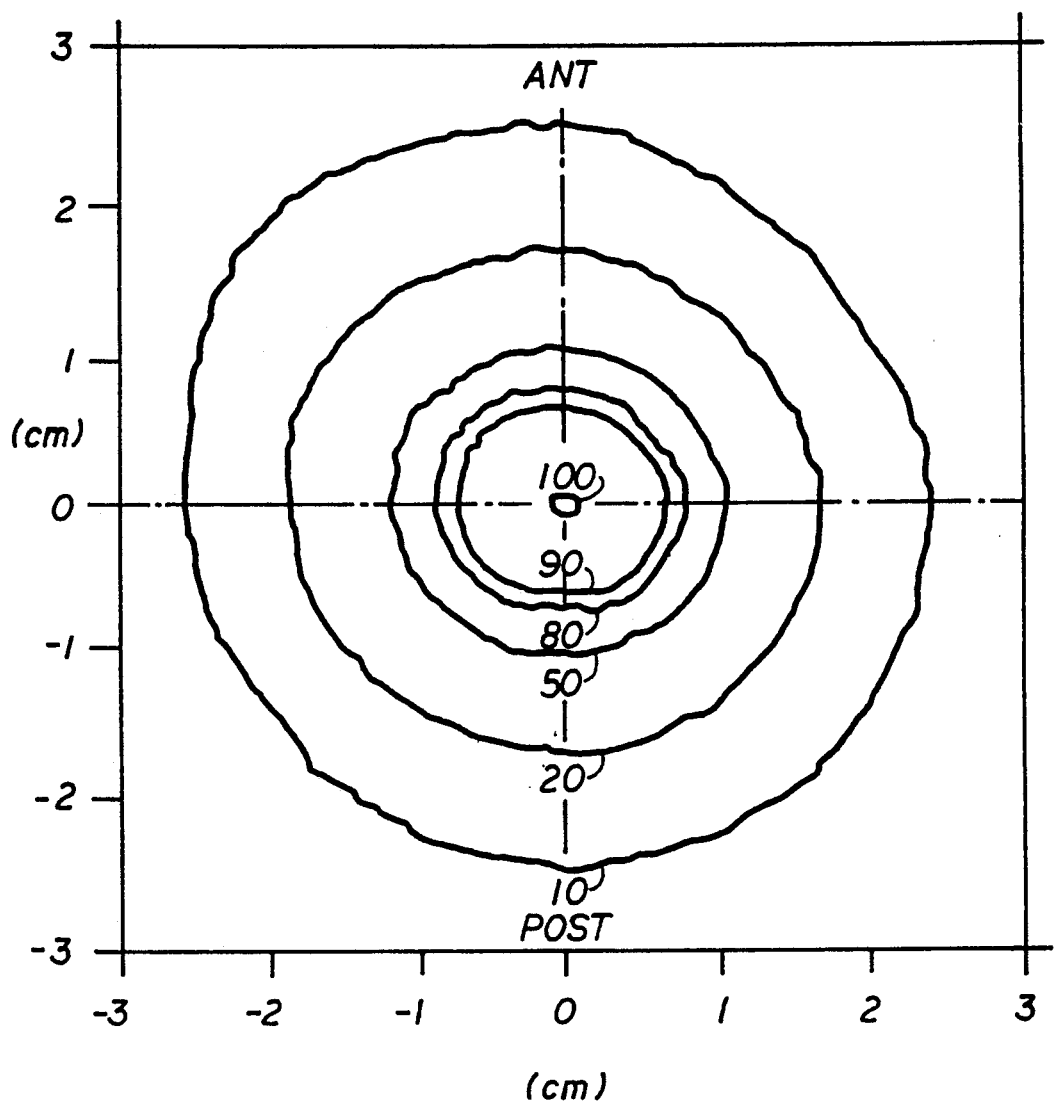
FIG. 6 is a graph depicting the transverse dose distributing produced by use of 35°, 60°, and 80° gantry angles with the 2 cm diameter collimator for a target point located near the center of the brain.
Figure 7:
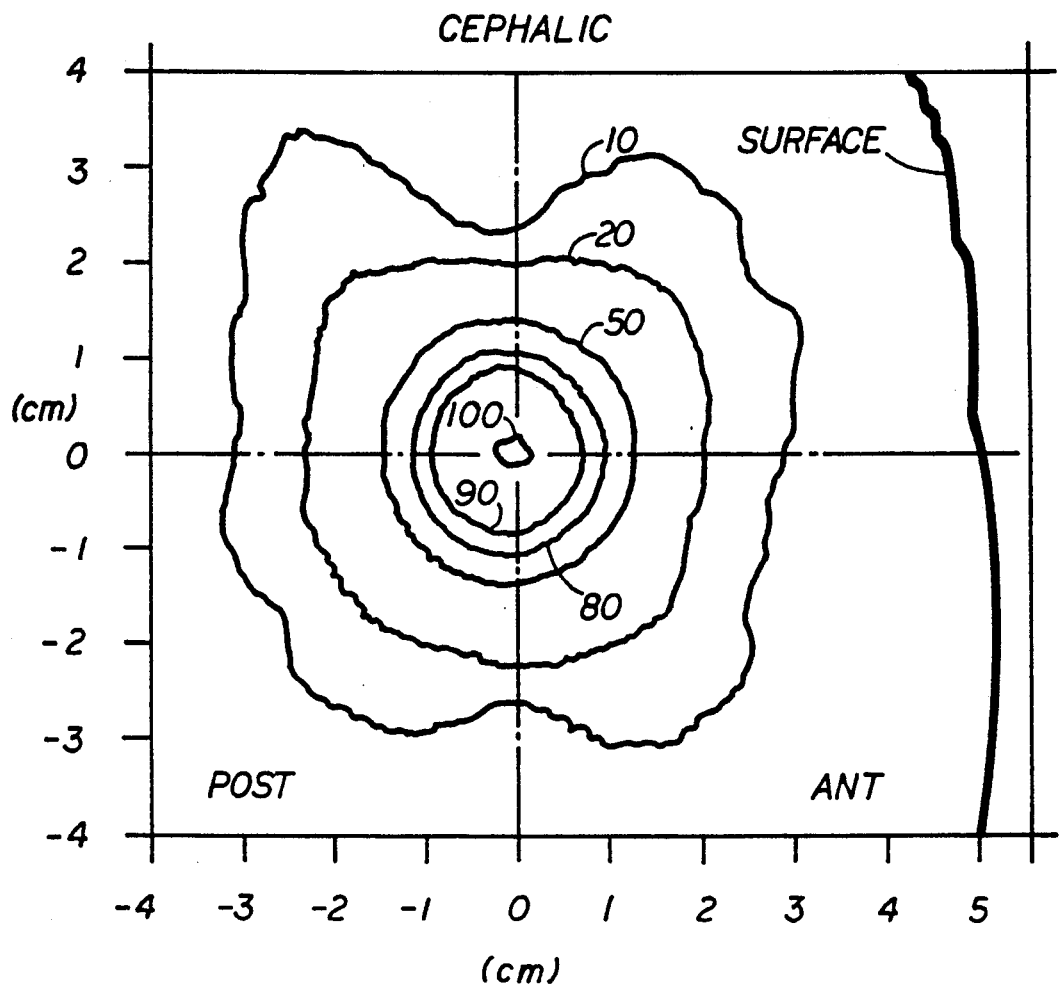
FIG. 7 is a graph depicting the dose distribution produced by use of 35°, 60°, and 80° gantry angles with the 2 cm diameter collimator for a target point in the right anterior quadrant of the brain.
Figure 8:
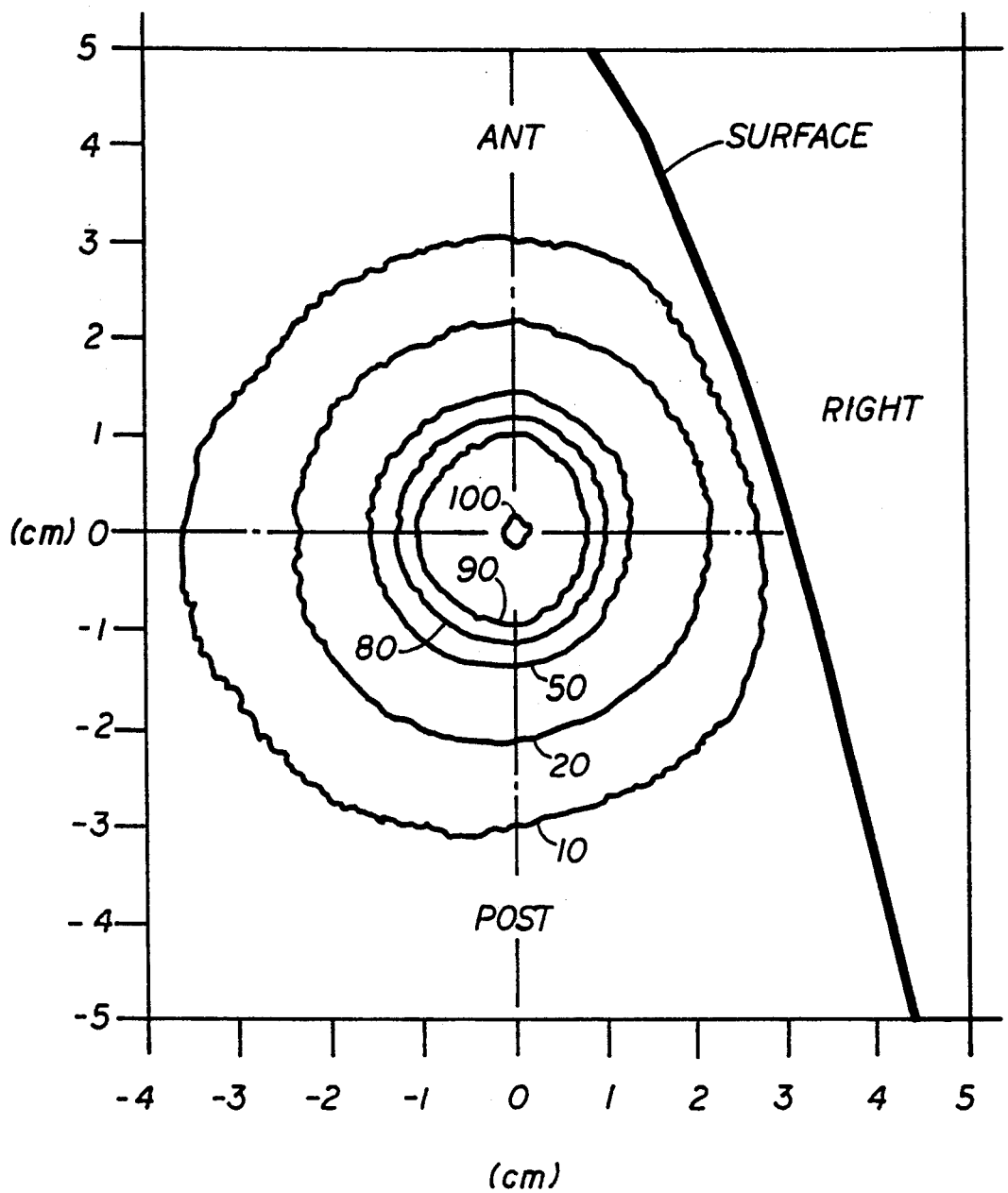
FIG. 8 is a graph depicting the transverse dose distribution produced by 35°, 60°, and 80° gantry angles with the 2 cm diameter collimator for a target point in the right anterior quadrant of the brain.

The coronal dose distribution was found to have the same general features as the sagittal plane. Dose distributions determined for a target point in the right anterior quadrant of the brain are presented in FIGS. 6 and 7 for the 2 cm diameter collimator. Measurements were also made for the two additional target points (left posterior quadrant and anterior of the brain center) using the 1, 2, and 3 cm collimators. For each collimator, the size of the high dose region did not change with target position and the minimum and maximum dose gradient out side the 90% dose level did not vary by more than 2 mm. The diameter of the 90% dose level was found to be 4 mm less than the collimator size and 2 mm less for the 80% dose level.

The positional error which is defined as the distance between the target point (pin) and the center of the high dose regions (90% or 80%) was established for the following points: center of the brain, right anterior quadrant, anterior region of sagittal plane, and left posterior quadrant. It should be pointed out that the positional error includes all errors due to localization and errors due to the delivery system. A total of 3 experimental runs were made for each target center listed above and a maximum positional error of 2 mm was found when CT localization was used and 1.0 mm when angiography was utilized. No increase in the positional error was noted when the RAND TM phantom was placed in the rotator chair after the alignment procedure was carried out.

Discussion

The rotational device described herein allows the precise delivery of radiation doses to small lesions in the brain with high positional accuracy. In addition, the system is less expensive, more simple to operate, and offers a higher degree of patient safety than other techniques employed with linear accelerators. A total time of about 10 minutes is required to prepare the linear accelerator for stereotactic therapy and approximately 45 minutes is spent in alignment of the rotator with respect to the radiation beam utilizing the radiographic method.

By employing specific gantry angles (35°, 60° and 80°), a spherical high dose region (90% and 80%) which is centered on the target point is created. The target volume diameter based on the 90% dose level is approximately 4 mm smaller than the collimator diameter and 2 mm smaller based on the 80% dose level. It was found that the space and size of the high dose region was independent of position in the brain. Based on test runs, the maximum distance between the center of the high dose volume and the target point was observed to be 2 mm. A sharp dose fall off outside the target volume was found for the range of collimators used (1 to 3 cm). The maximum distance from the edge of the high dose region and the 20% or 10% dose level is a function of collimator size and occurs in the general direction of the incoming radiation beams.

The invention is not limited to the specific embodiment or example described above. Modifications may be carried out within the scope of the invention which is limited only by the claims.

I claim:

1. An apparatus for rotating a patient during stereotactic radiosurgery adapted for use with a source of radiation that is stationary, comprising:
   (a) a frame;
   (b) a platform connected to said frame for rotating 360° about a vertical rotational axis;
   (c) means for rotating said platform about the vertical rotational axis;
   (d) a patient receiving means connected to said platform; and
   (e) means connected to the said platform and adapted for the stereotactic positioning of a patient's head with respect to the vertical rotational axis to permit intersection of the radiation from the source with the vertical rotational axis at the location of a target site in the head that is the subject of the radiosurgery, the positioning means comprising a horizontal bar having stereotactic locational indicia, a vertical bar having stereotactic locational indicia and means for holding a patient's head, each bar being adjustably attachable to said means for holding a patient's head.

2. The apparatus of claim 1, further comprising means for maintaining the adjusted patient's head in a stationary position.

3. The apparatus of claim 1, wherein said patient receiving means is a seat having a vertical support and a horizontal support.

* * * * *